United States Patent [19]
Machold et al.

[11] Patent Number: 5,611,775
[45] Date of Patent: Mar. 18, 1997

[54] METHOD OF DELIVERY THERAPEUTIC OR DIAGNOSTIC LIQUID INTO TISSUE SURROUNDING A BODY LUMEN

[75] Inventors: Timothy R. Machold, Moss Beach; Janine C. Robinson, Half Moon Bay; Mary B. Michaels; Motasim M. Sirhan, both of Sunnyvale, all of Calif.

[73] Assignee: Advanced Cardiovascular Systems, Inc., Santa Clara, Calif.

[21] Appl. No.: 238,904

[22] Filed: May 6, 1994

Related U.S. Application Data

[63] Continuation of Ser. No. 31,569, Mar. 15, 1993, abandoned.
[51] Int. Cl.⁶ .................................................. A61M 31/00
[52] U.S. Cl. .................................................. 604/53; 604/96
[58] Field of Search ........................... 604/96, 101, 265, 604/52, 53; 606/192, 194

[56] References Cited

U.S. PATENT DOCUMENTS

| | | | |
|---|---|---|---|
| 3,173,418 | 3/1965 | Baran | 604/101 X |
| 4,417,576 | 11/1983 | Baran | 604/101 X |
| 4,423,725 | 1/1984 | Baran et al. | 604/101 X |
| 4,994,033 | 2/1991 | Shockey et al. | 604/101 |
| 5,049,132 | 9/1991 | Shaffer et al. | 604/101 |
| 5,087,244 | 2/1992 | Wolinsky et al. | 604/53 |
| 5,213,576 | 5/1993 | Abiuso et al. | 604/96 |
| 5,236,413 | 8/1993 | Feiring | 604/21 |
| 5,295,962 | 3/1994 | Crocker et al. | 604/101 |

FOREIGN PATENT DOCUMENTS

| | | | |
|---|---|---|---|
| 9211895 | 7/1992 | WIPO | 604/101 |

Primary Examiner—Corrine M. McDermott
Attorney, Agent, or Firm—Heller Ehrman White & McAuliffe

[57] ABSTRACT

A catheter and method of using the catheter for the delivery of therapeutic or diagnostic liquid within a body lumen of a patient. The catheter has an outer inflatable member which has a wall with a plurality of apertures which eject therapeutic or diagnostic liquid in a jet-like form deep within the lumenal tissue adjacent to the outer inflatable member. In one embodiment the catheter has an inner inflatable member disposed within the outer inflatable member which upon inflation expands the outer tubular member so as to dilatate a stenotic region of a body lumen such as an artery. The inflatable member may be provided with proximal and distal ends which expand to larger diameters than the central inflatable section so as to seal the larger ends and prevent the loss of fluid.

13 Claims, 3 Drawing Sheets

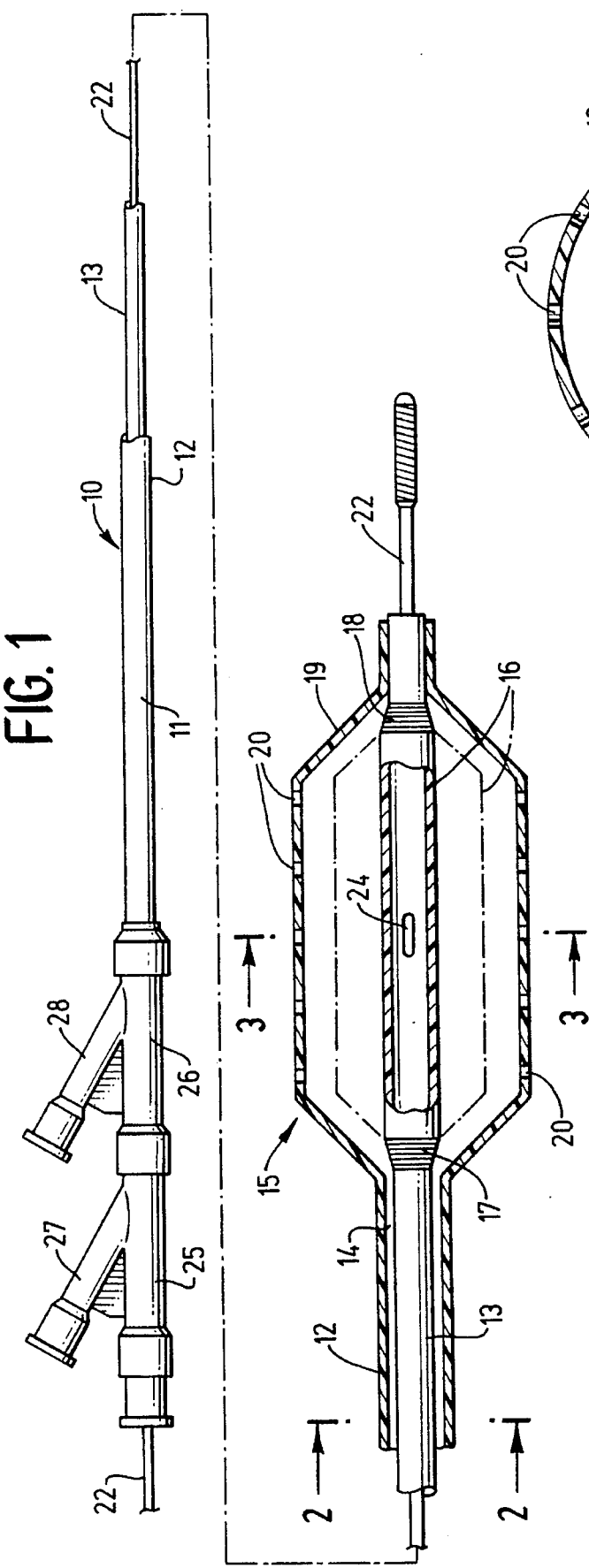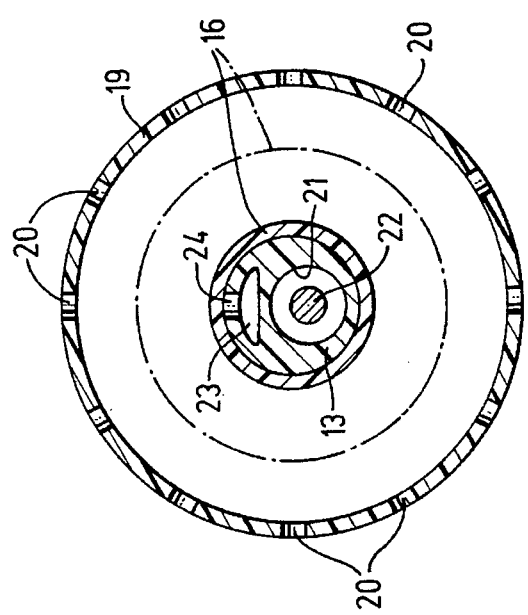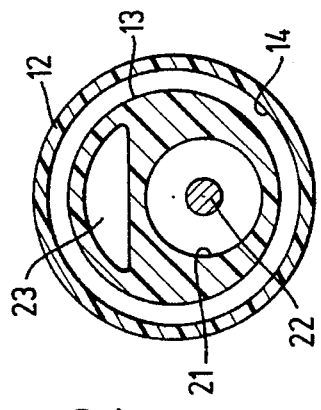

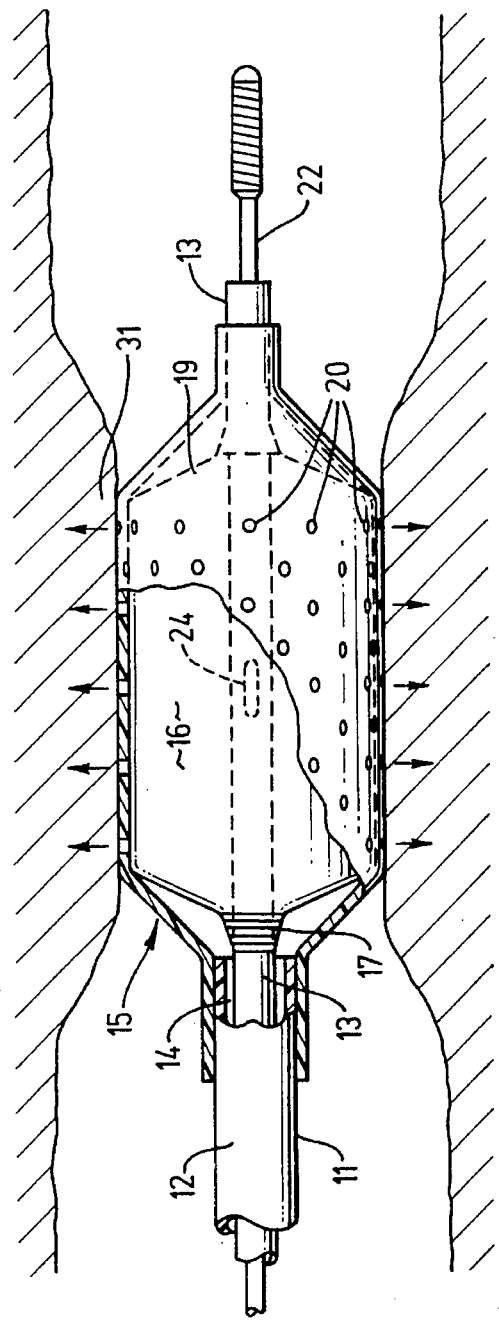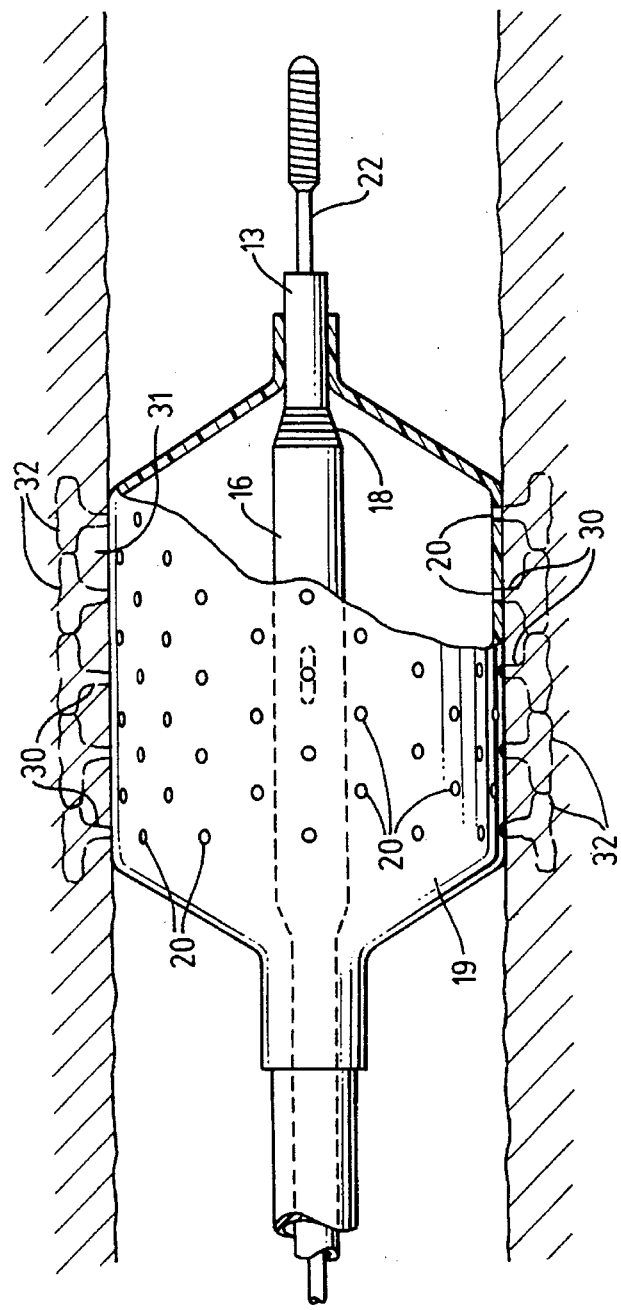

METHOD OF DELIVERY THERAPEUTIC OR DIAGNOSTIC LIQUID INTO TISSUE SURROUNDING A BODY LUMEN

This is a continuation of application Ser. No. 08/031,569 filed on Mar. 15, 1993, now abandoned.

BACKGROUND OF THE INVENTION

This invention is directed to the delivery of a liquid containing therapeutic or diagnostic material to a desired site within a patient's body. The invention has particular application to procedures in coronary or peripheral arteries such as percutaneous transluminal coronary angioplasty (PTCA).

PTCA is a widely used procedure for the treatment of coronary heart disease. In this procedure, a balloon dilatation catheter is advanced into the patient's coronary artery and the balloon on the catheter is inflated within the stenotic region of the patient's artery to open up the arterial passageway and thereby increase the blood flow through the artery.

One type of catheter frequently used in PTCA procedures is an over-the-wire type balloon dilatation catheter. Commercially available over-the-wire type dilatation catheters include the SIMPSON ULTRA LOW PROFILE®, the HARTZLER ACX®, the HARTZLER ACX II®, the PINKERTON 0.018™ and the ACS TEN™ balloon dilatation catheters sold by the assignee of the present application, Advanced Cardiovascular Systems, Inc. (ACS).

Coronary and peripheral angioplasty procedures have met with considerable success and have greatly reduced the need for by-pass surgery. However, in some instances the physical dilatation of the stenosis during the angioplasty procedure has been found to be inadequate by itself to effectively treat the stenotic region. Restenosis, the reforming of plaque in an artery, is a problem in over 30% of the coronary angioplasty procedures, and in many cases the restenosis is severe enough to require redilatation. Restenosis is believed to occur due to the proliferation of smooth muscle cells in the region of the dilatated artery.

It has been proposed to use heparin and other types of therapeutic agents in the stenotic regions of a patient's coronary arteries in order to reduce the incidence of restenosis. It has also been suggested to utilize therapeutic agents such as urokinase, streptokinase and tissue plasminogen activator (TPA) to treat thrombus in stenotic regions. Other drugs and therapeutic agents have also been suggested. However, the systemic use of therapeutic and diagnostic agents is not very desirable because the patient's entire body must be medicated to a very high level in order to treat or diagnose a small region in the patient's vasculature and frequently these therapeutic and diagnostic materials can be toxic at the levels needed for effective treatment or diagnosis.

Site specific delivery systems for drugs, therapeutic agents and diagnostic agents through catheters are known but such systems have not always been effective. Usually, only the surface tissue is treated. Wolinsky et al. in *Journal of the American College of Cardiology*, Vol 17, No. 6, 1991, 174–178; *Journal of the American College of Cardiology*, Vol. 15, No. 2, 1990, 475–481; *Journal of Interventional Cardiology*, Vol. 2, No. 4, 1989,219–228; and Goldman et al. in *ATHEROSCLEROSIS*, 65 (1987) 215–225, describe a therapeutic or diagnostic fluid delivery system which includes a perforated balloon to infuse therapeutic or diagnostic fluids into artery walls. See also U.S. Pat. No. 5,087,244 (Wolenski). Apparently, in the procedures described in the above references, liquid is maintained between the surface of the balloon and the adjacent tissue and the inflation of the balloon creates a relatively high fluid pressure and forces the fluid to permeate into the arterial tissue. However, during these procedures it has been found that a substantial amount of fluid is frequently driven away from the delivery site and thereby lost, apparently due to fluid leaking between the balloon and the stenosis. Ring type balloons have been disposed adjacent both ends of the perforated balloons in an attempt to minimize the loss of fluid, such as shown in U.S. Pat. No. 4,636,195 and U.S. Pat. No. 4,824,436, but the additional inflation lumens needed to inflate the ring balloons complicate the catheter structure and thus the manufacturability of the product. These designs also significantly increase the profile of the shaft and greatly limit the usefulness of the catheter. Moreover, because the inflated balloons of these designs block arterial passageways, the period for fluid delivery must necessarily be quite short, particularly in a patient's coronary arteries.

What has been needed and heretofore unavailable is a means to deliver therapeutic agents, diagnostic agents and the like deep within tissue without both damage to the tissue and significant systemic loss of the fluid material being delivered. Of particular need is a means to deliver such a fluid so as to provide long term availability of the delivered therapeutic or diagnostic material without significant loss thereof. The present invention satisfies these and other needs.

SUMMARY OF THE INVENTION

This invention is directed to a catheter and method for the site specific delivery of a liquid containing therapeutic or diagnostic materials within a patient's body, and particularly to such a catheter and method which provides enhanced retention of the fluid delivered to the site for a prolonged availability of the fluid at the site.

The catheter of the invention generally includes an elongated catheter shaft having at least one inner lumen extending therein, an outer inflatable member on a distal extremity of the catheter shaft having an interior in fluid communication with an inner lumen within the catheter shaft and an adapter on the proximal end of the catheter shaft for directing fluids through the inner lumen extending through the catheter shaft to the interior of the inflatable member. The wall forming the outer inflatable member has a plurality of small apertures so that when the inflatable member is filled with therapeutic or diagnostic liquids under relatively high pressure, liquid is ejected from she apertures in the form of jets having sufficient velocity to penetrate into tissue surrounding the outer inflatable member. The apertures in the wall of the outer inflatable member may generally range from about 10 to about 100 microns, preferably about 20 to about 80 microns, in effective diameter. The aperture density within the wall ranges from about 15 to about 100 holes per $cm^2$ of surface area. To obtain the desired penetration into adjacent tissue the fluid velocity should range from about 0.5 to about 15 meters/sec, preferably about 1 to about 10 meters/sec. With the above aperture sizes, the requisite velocity provides a volume flow rate from about 0.0015 to about 0.05 ml/sec per hole. The pressure within the outer inflatable member to obtain the desired jet penetration into adjacent tissue forming the body, or the tissue of any organ beyond the tissue forming body lumen, will vary depending upon the viscosity of the fluid to be delivered and the nature of the adjacent tissue. Typically pressure within the inflatable member ranging from about 0.75 to about 10 atmospheres, preferably about 1 to about 8 atmospheres has been found suitable. The duration of the balloon inflation for effective penetration by the liquid jet is dependent upon the amount of therapeutic or diagnostic material needed and the concentration of such material in the delivery liquid. The duration of the jet-like flow delivery is usually less than one minute, and frequently less than 30 seconds, which is short enough for most coronary applications. One of the advantages of the invention is the ability to deliver a relatively large volume of liquid for long term treatment over a relatively short period of time with little disruption of normal bodily functions and relatively little loss of the fluid.

In one preferred embodiment of the catheter, the catheter shaft has an outer tubular member and an inner tubular member with an annular lumen defined between these tubular members which is adapted to deliver therapeutic or diagnostic fluids to the interior of an outer inflatable member on the distal extremity of the catheter shaft. The inner tubular member has two inner lumens, one of which is adapted to slidably receive a guidewire and the other which is adapted to direct inflation fluid into the interior of an inner inflatable member disposed within the outer inflatable member. An inner inflatable member is preferably secured at both of its ends to the distal extremity of the inner tubular member. The outer inflatable member, which has an array of apertures through its wall, is disposed about the inner inflatable member with a distal end secured to the distal end of the inner tubular member. The proximal end of the outer inflatable member may form all or a part of the outer tubular member or may be a short skirt which is secured to the distal end of the outer tubular member.

The use of the above-described preferred embodiment entails advancing the catheter through a patient's vascular system over a guidewire in much the same fashion as an over-the-wire balloon angioplasty catheter is advanced into a patient's arterial system. Once the inflatable assembly, which includes the inner and outer inflatable members, is properly positioned across the fluid delivery site, the inner inflatable member is inflated to expand the outer inflatable member and dilatate the stenotic region within the artery. After the dilatation, the inner inflatable member is deflated. Therapeutic or diagnostic liquid is directed through the annular lumen between the inner and outer tubular members into the interior of the outer inflatable member. The pressure of the liquid is increased to a level high enough to cause jets of the fluid to be ejected from the apertures in the wall of the outer inflatable member and to penetrate well into the tissue adjacent the outer inflatable member with relatively little loss of fluid. The outer inflatable member is inflated to a size so that its wall is immediately adjacent to the stenosis or other tissue to which the fluid is to be delivered. There is no need to expand the inflatable member to further dilate the stenotic region. This embodiment is particularly suitable for coronary procedures because both the dilatation of the stenosis and the delivery of the therapeutic fluid are performed with the same catheter, and there is no need to withdraw the catheter until both procedures are completed.

The catheter system and method of the invention can effectively deliver therapeutic or diagnostic liquids into the tissue adjacent the balloon as well as tissue far beyond the body lumen walls. The jets of liquid provide much deeper and more effective penetration of the liquid into the surrounding tissue mass than previously known methods and can result in a greater retention of the liquid within the tissue by creating a reservoir of the fluid therein. The jet penetration of the liquid into the tissue also results in much less loss of liquid between the outer inflatable member and the stenosis. Moreover, much higher concentrations of therapeutic and diagnostic materials in the carrier liquid can be safely used with the catheter of the present invention because there is much less systemic loss of the liquid when the delivery is by means of liquid jet and because of the enhanced retention of the delivered liquid. Fluid from a reservoir of such fluid formed within the tissue will slowly permeate into adjacent tissue providing prolonged delivery of the therapeutic or diagnostic liquid. While the invention is particularly suitable for the delivery of drugs which prevent the proliferation of smooth muscle cells, such as heparin, to angioplasty sites after the angioplasty procedure in order to prevent or minimize restenosis, the invention may also be used to deliver therapeutic or diagnostic liquids to other body sites such as the prostatic urethra, e.g. to deliver therapeutic liquids to the prostate gland in the treatment of benign or malignant hyperplasia. Therapeutic agents which may be used include vasodilators, anti-thrombotics, anti-platelet agents, angiotensin converting enzyme inhibitors, cytostatic and cytotoxic agents and chemotherapeutic agents. Agents which may be used for preventing or minimizing restenosis include colchicine, heparin, dexamethasone, angiopeptin, methotrexate, dipyridamole, which may be used in suitable pharmaceutically acceptable liquid carriers, as bioerodible microparticles, in microencapsulated particles or in other suitable forms.

These and other advantages of the invention will become more apparent from the following detailed description of the invention, when taken in conjunction with the accompanying exemplary drawings.

BRIEF DESCRIPTION OF THE DRAWINGS

FIG. 1 is an elevational view, partially in section, of a catheter embodying features of the invention.

FIG. 2 is a transverse cross-sectional view of the catheter shown in FIG. 1 taken along the lines 2—2.

FIG. 3 is a transverse cross-sectional view of the catheter shown in FIG. 1 taken along the lines 3—3.

FIG. 4 is a schematic elevational view, partially in section of the distal end of the catheter shown in FIG. 1 with the outer inflatable member being expanded by the inflated inner inflatable member to dilate a stenosis.

FIG. 5 is a schematic elevational view, partially in section, of the distal end of the catheter shown in FIG. 1 with the outer inflatable member in the inflated condition with jets of liquid projecting into adjacent tissue.

DETAILED DESCRIPTION OF THE INVENTION

Figure 6:
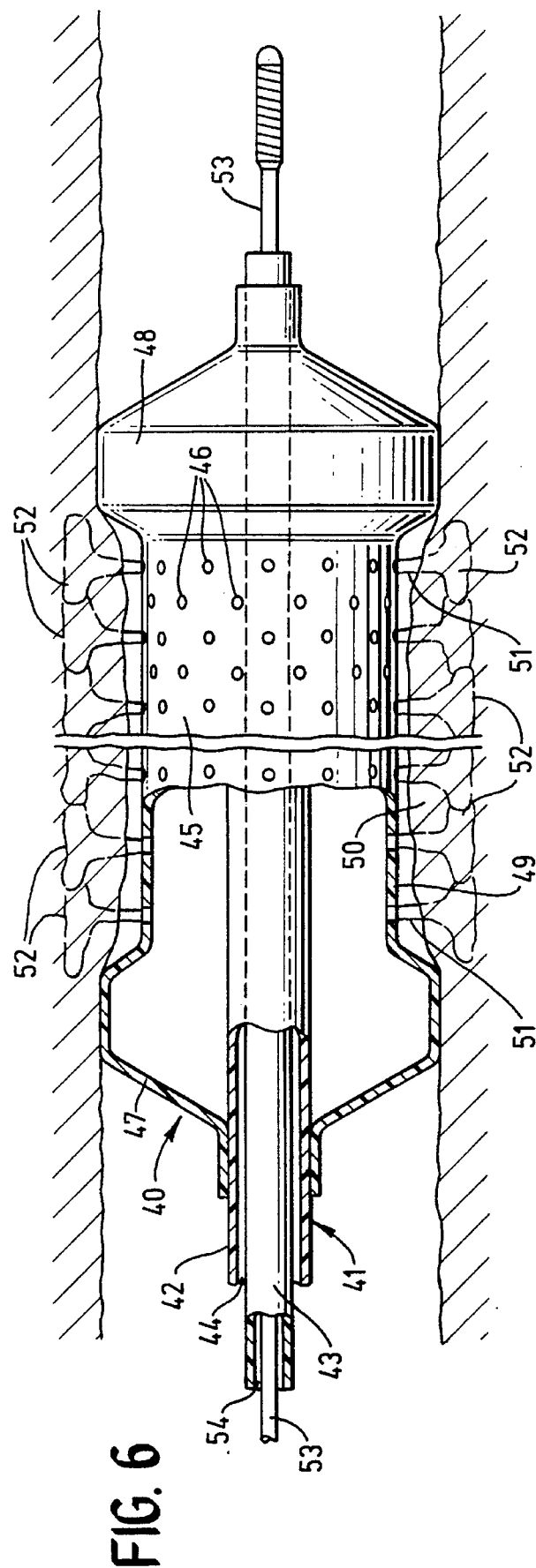
FIG. 6 is a schematic elevational view, partially in section, of the distal end of an alternative catheter for delivering fluid containing therapeutic or diagnostic materials to adjacent tissue.

FIG. 1 schematically illustrates a dilatation catheter 10 embodying features of the invention. The catheter 10 generally comprises an elongated catheter shaft 11 including an outer tubular member 12, an inner tubular member 13, an annular lumen 14 extending between the inner and outer tubular members and an inflation assembly 15 on the distal extremity of the catheter shaft. The inflation assembly 15 includes an inner inflatable member 16 which is secured to the inner tubular member 13 which extends therethrough by means of a suitable adhesive or by gold bands 17 and 18 which can be radiopaque markers to facilitate the fluoroscopic observation of the inner inflatable member during the intravascular procedure. An outer inflatable member 19, having a plurality of holes 20 in the wall thereof, is disposed about the inner inflatable member 16 and is secured by its distal end to the distal end of the inner tubular member 13 and by its proximal end to the distal end of the outer tubular member 12 of the catheter shaft 11. The holes 20 may take a variety of transverse shapes but preferably are either oval shaped or circular. The ends of the outer inflatable member 12 may be secured by heat bonding or by suitable adhesives.

The inner tubular member 13, as best shown in FIGS. 2 and 3, has two inner lumens, a first inner lumen 21 which is adapted to slidably receive a guidewire 22 and a second inner lumen 23 which is adapted to direct inflation fluid to the interior of the inner inflatable member 16 through inflation port 24.

Two two-arm adapters 25 and 26 are connected in series to the proximal end of the catheter shaft 11. Arm 27 of adapter 25 is in fluid communication with the inner inflation lumen 23, whereas arm 28 of adapter 26 is in fluid communication with the annular lumen 14.

The catheter 10 may be advanced to a desired location within a patient's arterial system utilizing conventional techniques for the placement of an over-the-wire balloon angioplasty catheter within a patient's coronary or peripheral artery. To facilitate the advancement of the catheter of the invention into a patient's coronary artery using conventional techniques, a guiding catheter (not shown) having a preshaped distal tip is first percutaneously introduced into the cardiovascular system of a patient by means of the Seldinger technique through the brachial or femoral arteries. The guiding catheter is advanced until its preshaped distal tip is disposed within the aorta adjacent the ostium of the desired coronary artery, and it is twisted or torqued from its proximal end, which extends out of the patient, to guide its distal tip into the ostium of the desired coronary artery. Guidewire 22 is usually inserted into the guidewire receiving inner lumen 21 of the inner tubular member 13 before the catheter 10 is introduced into the patient's vascular system and then both the guidewire and the catheter are introduced into and advanced through the guiding catheter to its distal tip. The guidewire 22 is first advanced out the seated distal tip of the guiding catheter and through the desired coronary artery until the distal end of the guidewire extends beyond the lesion to be dilatated. The catheter 10 is then advanced out of the distal tip of the guiding catheter, over the previously advanced guidewire 22, until the inflatable assembly 15 on the distal extremity of catheter 10 is properly positioned across the lesion to be dilatated in the coronary artery.

Once the inflatable assembly is properly positioned across the stenosis, inflation fluid is directed through the arm 27 of adapter 25 by means of a suitable inflation device (not shown) into the inner inflation lumen 23 of the inner tubular member 13 to perform a dilatation as shown in FIG. 4. The inner inflatable member 16, which is preferably formed of material exhibiting elastic expansion, inflates, expanding the outer inflatable member 19. The expansion continues until the stenosis is dilatated. Upon completion of the dilatation, the inner inflatable member 16 is then deflated. A liquid containing one or more therapeutic or diagnostic agents is then introduced through arm 28 of adapter 26 into the annular lumen 14 by means of a syringe type device, such as the inflation device used to inflate the inner inflatable member 16, where it is directed to the interior of the outer inflatable member 19. The pressure of the therapeutic or diagnostic liquid within the outer inflatable member 19 is increased to the level where the cylindrical wall of the outer inflatable member 19 is expanded closely adjacent to or in contact with the arterial wall and discrete jets 30 of the therapeutic or diagnostic fluid are ejected out of the apertures 20 well into the tissue of the previously dilatated stenosis 31 as shown in FIG. 5. There need be little or no expansion of the previously dilatated stenotic region 31 by the outer inflatable member 19. The injection period will be determined by the amount of therapeutic or diagnostic fluid which is to be delivered, the size of the apertures 20 in the wall of the outer inflatable member 19 and the pressure applied to the therapeutic or diagnostic fluid. The fluid delivery in discrete liquid jets has been found to be effective throughout the arterial wall and even to regions well outside the tunica adventitia of the artery. Preferably, a body or reservoir of the therapeutic or diagnostic liquid 32 is formed in the tissue spaced from the body lumen which allows the fluid to slowly permeate or infuse into the surrounding tissue thereby providing delivery of the diagnostic or therapeutic material over a long period. A suitable syringe type inflation device which has been found suitable for inflating the inner inflatable member 16 and for delivering the therapeutic or diagnostic liquid to the interior of the outer inflatable member in sufficient amounts and at sufficient pressure is the Indeflator® which is available from the assignee of the present application, Advanced Cardiovascular Systems, Inc. Other inflation devices may be used.

The materials of construction for the catheter of the invention may be selected from conventional materials and conventional methods of making the catheter may be employed. The inner and outer tubular members may be extruded polyethylene. The inner inflatable member may be formed from latex or an elastomer or an olefinic ionomer such as Surlyn® sold by E. I. duPont, deNemours & Co. which is elasticly expandable up to a first pressure level and is relatively non-compliant at pressures above the first level. A presently preferred ionomer is described in copending application Ser. No. 07/758,630, filed Sep. 12, 1991, which is incorporated herein by reference. A suitable latex inflatable member is available from Nolato Medical Company which has an ID of 0.033 inch and a wall thickness of about 0.006 inch. The outer inflatable member may be formed from conventional inelastic dilatation balloon materials such as polyvinyl chloride, polyethylene, polyethylene terephthalate and the olefinic ionomers described above. Plastic to plastic bonding may be effected by heat bonding, heat shrinking or by a suitable adhesive.

FIG. 6 illustrates an alternative embodiment of the invention. As shown, the catheter 40 generally comprises an elongated catheter shaft 41 including an outer tubular member 42, an inner tubular member 43, an annular lumen 44 extending between the inner and outer tubular members and an inflatable member 45 on the distal extremity of the catheter shaft. The inflation member 45 has an interior in fluid communication with the annular lumen 44 and a distal end which is secured to the distal end of the inner tubular member 43 which extends therethrough by suitable means, e.g. heat bonding or an adhesive. The inflatable member 45 has a plurality of holes 46 in the wall thereof, as in the previously discussed embodiments, to eject liquid containing diagnostic or therapeutic material in a plurality of jet-like streams. This embodiment may also be provided with an inner inflatable member and an inflation lumen as in the previously discussed embodiments. The inflatable member 45 is provided with end sections 47 and 48 which expand upon inflation to a larger diameter than the central section 49 which is provided with the apertures 46 in order to seal off the central portion of the inflatable member 45 to prevent loss of fluid. The length of the central section 49 is preferably at least as long as the stenosis 50 to be treated or diagnosed so that the end sections 47 and 48 seal against healthy tissue of the arterial wall. Generally, it is preferred that the end sections expand at least 5%, preferably at least 10% greater than the central section 49 to provide adequate pressure against the arterial wall or stenotic material for effective sealing. The end sections 47 and 48 may be formed with larger diameters when the inflatable member is formed or these sections may be treated to expand more when inflated such as described in the above-mentioned copending application Ser. No. 07/758,630, filed on Sep. 12, 1991 which is incorporated herein by reference. The fluid ejected from the apertures 46 flows in a jet-like form 51 deep into the adjacent tissue and preferably forms a body of fluid 52 which slowly seeps into adjacent tissue providing long term availability. The catheter 40 is advanced into a desired position within the patient's vasculature over guidewire 53 which is slidably disposed within inner lumen 54 extending within inner tubular member 43. While not shown in the drawing, this embodiment may have a dual lumen inner tubular member and a second inflatable member as described in the previous embodiment and the catheter so modified may be operated in essentially the same manner as previously described.

In another preferred embodiment of the invention, the catheter is provided with perfusion capabilities in order to facilitate long term delivery of therapeutic or diagnostic fluids. The catheter may be essentially the same catheter as shown in FIGS. 1–3 except that the inner tubular member 13 and the outer tubular member 12 are secured together in a distal portion of the catheter proximal to the inflatable member 19 as described in U.S. Pat. No. 4,892,519 (Songer et al.) and copending application Ser. No. 07/700,617, filed May 15, 1991, entitled Low Profile Dilatation Catheter (Sirhan et al.). These references are incorporated herein by reference. As described in these references one or more proximal perfusion ports extend through the secured walls of the inner and outer tubular members and are in fluid communication with the inner lumen 21. One or more distal perfusion ports may also be provided which are likewise in fluid communication with the inner lumen 21 of the inner tubular member 13. When using this embodiment the outer balloon is inflated to the desired diameter so that the outer surface of the balloon is immediately adjacent to the arterial region where the fluid is to be delivered. The inner balloon is then slowly inflated with inflation fluid to cause the ejection of the therapeutic or diagnostic fluid through the small apertures in the wall of the outer balloon member at sufficient velocity to cause the fluid to form a high velocity jet which penetrates into the tissue of the arterial wall in the manner previously described. The number of apertures which are exposed to allow fluid discharge is controlled to provide the desired total flow. Upon the initial inflation of the outer balloon, flow of blood through the arterial passageway is effectively blocked and as a result thereof blood is forced to flow through the proximal perfusion ports, through the inner lumen 21 and out the distal perfusion ports. It is this perfusion of oxygenated blood which prevents or minimizes ischemic conditions in the artery downstream from the catheter. Long term fluid delivery of up to 2 or more hours are possible with this system having perfusion capabilities.

While the invention has been described herein primarily with reference to presently preferred embodiments, those skilled in the art will recognize that various modifications and improvements may be made to the invention without departing from the scope thereof.

What is claimed is:

1. A method of delivering therapeutic or diagnostic material in liquid form into tissue surrounding a body lumen of a patient comprising:
   a) providing a catheter with:
      a catheter shaft having proximal and distal ends and at least one inner lumen extending therein;
      an inflatable member on a distal portion of the catheter shaft having an interior in fluid communication with the inner lumen extending within the catheter shaft and a wall with a plurality of small apertures extending therethrough; and
      means to direct therapeutic or diagnostic material in liquid form from the inner lumen to the interior of the inflatable member;
   b) advancing the catheter through a body lumen of a patient until the inflatable member is disposed at a site therein where the therapeutic or diagnostic liquid is to be delivered; and
   c) directing therapeutic or diagnostic liquid through the inner lumen into the interior of the inflatable member so that the liquid is ejected from the plurality of small apertures in the wall of the inflatable member in the form of a corresponding plurality of individual streams, each individual stream having a velocity capable of piercing the tissue surrounding the body lumen so that the liquid enters the tissue as a stream, to form a resevoir of therapeutic or diagnostic material within the tissue surrounding the body lumen.

2. The method of claim 1 wherein the liquid velocity through the apertures is about 0.5 to about 15 meters/sec.

3. The method of claim 1 wherein the liquid velocity through the apertures is about 3 to about 8 meters/sec.

4. The method of claim 1 wherein the volumetric flow rate per aperture ranges from about 0.0015 to about 0.05 ml/sec.

5. A method of dilating a blood vessel and delivering diagnostic or therapeutic liquid to tissue of the blood vessel, comprising:
   a) advancing within the blood vessel an elongated catheter which comprises:
      an elongated catheter shaft having proximal and distal extremities and first and second lumens extending therein;
      an outer inelastic inflatable member on a distal extremity of the catheter shaft with an interior in fluid communication with the first lumen within the catheter shaft and with a wall having a plurality of small apertures;
      an inner inflatable member disposed within the outer inflatable member with an interior in fluid communication with the second inner lumen extending within the catheter shaft;
      means on the proximal extremity of the catheter shaft to direct inflation fluid through the second inner lumen within the shaft to the interior of the inner inflatable member; and
      means on the proximal extremity of the catheter shaft to direct therapeutic or diagnostic liquid through the first inner lumen within the shaft to the interior of the outer inflatable member;
   b) positioning the catheter within the blood vessel so that the inner and outer inflatable members are disposed within a desired stenotic location within the blood vessel;

c) directing inflation fluid through the second inner lumen within the shaft into the interior of the inner inflatable member to inflate the inner inflatable member and thereby expand the outer inflatable member sufficiently to dilate the stenotic region of the blood vessel;

d) withdrawing inflation fluid through the second inner lumen to deflate the inner inflatable member; and e) directing diagnostic or therapeutic liquid through the first inner lumen within the shaft into the interior of the outer inflatable member to inflate the outer inflatable member with sufficient pressure so that diagnostic or therapeutic liquid is ejected through the small apertures in the wall of the outer inflatable member in a jet-like flow of individual streams, each individual stream having sufficient velocity to pierce the tissue in the stenotic region of the blood vessel, to form a resevoir of therapeutic or diagnostic material within the tissue surrounding the body lumen.

6. The method of claim 5 wherein the volumetric flow rate of liquid being discharged out the apertures ranges from about 0.0015 to about 0.05 ml/sec.

7. The method of claim 5 wherein the velocity of the liquid being discharged from the apertures in the form of liquid jets ranges from about 3 to about 8 meters/sec.

8. The method of claim 5 wherein the wall of the outer inflatable member has about 15 to about 100 apertures per $cm^2$ of wall surface.

9. The method of claim 5 wherein the velocity of the jet-like flow is about 0.5 to about 15 meters/sec.

10. A method of delivering diagnostic or therapeutic fluids to tissue of the blood vessel, comprising:

a) advancing within the blood vessel an elongated catheter which comprises
   an elongated catheter shaft having proximal and distal extremities and first and second lumens extending therein,
   an outer inflatable member on a distal extremity of the catheter shaft with an interior in fluid communication with the first lumen within the catheter shaft and with a wall having a plurality of small apertures,
   an inner inflatable member disposed within the outer inflatable member with an interior in fluid communication with the second inner lumen extending within the catheter shaft,
   means on the proximal extremity of the catheter shaft to direct inflation fluid through the second inner lumen within the shaft to the interior of the inner inflatable member, and
   means on the proximal extremity of the catheter shaft to direct therapeutic or diagnostic liquid through the first inner lumen within the shaft to the interior of the outer inflatable member;

b) positioning the catheter within the blood vessel so that the inner and outer inflatable members are disposed at a desired stenotic location within the blood vessel;

c) directing diagnostic or therapeutic liquid through the first inner lumen within the shaft into the interior of the outer inflatable member;

d) directing inflation fluid through the second inner lumen to the interior of the inner inflatable member to expand the inner inflatable member to create sufficient pressure within the outer inflatable member so that diagnostic or therapeutic liquid is ejected through the small apertures in the wall of the outer inflatable member in a jet-like fluid flow of individual streams, each individual stream having velocity sufficient to pierce the tissue surrounding the outer inflatable membe, to form a resevoir of therapeutic or diagnostic material within the tissue surrounding the body lumen; and e) withdrawing inflation fluid through the second inner lumen to deflate the inner inflatable member.

11. The method of claim 10 wherein the velocity of the jet-like flow is about 0.5 to about 15 meters/second.

12. The method of claim 10 wherein the volumetric flow rate of liquid being discharged out the apertures in jet-like fluid flow ranges from about 0.0015 to about 0.05 ml/sec.

13. The method of claim 10 wherein the velocity of the jet-like flow is about 3 to about 8 meters/sec.

* * * * *

UNITED STATES PATENT AND TRADEMARK OFFICE
CERTIFICATE OF CORRECTION

PATENT NO.    : 5,611,775
DATED         : March 18, 1997
INVENTOR(S)   : T. Machold et al.

It is certified that error appears in the above-identified patent and that said Letters Patent is hereby corrected as shown below:

On the title page, item [54] and column 1, line 1, change "DELIVERY" to --DELIVERING--.

Signed and Sealed this

Twenty-ninth Day of September, 1998

Attest:

BRUCE LEHMAN

*Attesting Officer*                    *Commissioner of Patents and Trademarks*